United States Patent
Matsutani et al.

(10) Patent No.: US 11,464,722 B2
(45) Date of Patent: Oct. 11, 2022

(54) FIRST AGENT FOR OXIDATION HAIR DYE OR HAIR DECOLORIZING AGENT

(71) Applicant: Henkel AG & Co. KGaA, Duesseldorf (DE)

(72) Inventors: Akira Matsutani, Tokyo (JP); Shoko Nagafuchi, Tokyo (JP); Shoji Machida, Tokyo (JP); Koji Takata, Tokyo (JP); Maki Miyamoto, Tokyo (JP)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/042,783

(22) PCT Filed: Sep. 26, 2018

(86) PCT No.: PCT/JP2018/035759
§ 371 (c)(1),
(2) Date: Sep. 28, 2020

(87) PCT Pub. No.: WO2019/187232
PCT Pub. Date: Oct. 3, 2019

(65) Prior Publication Data
US 2021/0015729 A1    Jan. 21, 2021

(30) Foreign Application Priority Data
Mar. 30, 2018 (JP) .............................. JP2018-068684

(51) Int. Cl.
| | | |
|---|---|---|
| *A61Q 5/10* | (2006.01) | |
| *A61K 8/362* | (2006.01) | |
| *A61K 8/19* | (2006.01) | |
| *A61K 8/34* | (2006.01) | |
| *A61K 8/41* | (2006.01) | |
| *A61Q 5/08* | (2006.01) | |

(52) U.S. Cl.
CPC ................ *A61K 8/362* (2013.01); *A61K 8/19* (2013.01); *A61K 8/342* (2013.01); *A61K 8/416* (2013.01); *A61Q 5/08* (2013.01); *A61Q 5/10* (2013.01); *A61K 2800/4322* (2013.01); *A61K 2800/596* (2013.01)

(58) Field of Classification Search
CPC . A61Q 5/10; A61Q 5/08; A61K 8/342; A61K 8/416; A61K 2800/4322; A61K 8/92; A61K 2800/596; A61K 8/362
USPC .............................................................. 8/405
See application file for complete search history.

(56) References Cited

U.S. PATENT DOCUMENTS

| | | | |
|---|---|---|---|
| 7,951,209 B2 | 5/2011 | Cotteret | |
| 2010/0021396 A1* | 1/2010 | Kleen | .................... A61K 8/466 424/47 |
| 2015/0053228 A1* | 2/2015 | Bonauer | .............. A45D 19/012 132/208 |
| 2016/0256373 A1* | 9/2016 | Matsutani | ................ A61K 8/22 |
| 2017/0202763 A1* | 7/2017 | Manneck | ................ A61Q 5/10 |
| 2017/0246094 A1* | 8/2017 | Dreher | ..................... A61Q 5/10 |
| 2017/0340537 A1* | 11/2017 | Morishita | ................ A61K 8/39 |
| 2018/0021601 A1 | 1/2018 | Kerl et al. | |

FOREIGN PATENT DOCUMENTS

| | | |
|---|---|---|
| EP | 1326577 B2 † | 7/2003 |
| JP | 2004-519446 A | 7/2004 |
| JP | 2005-23023 A | 1/2005 |
| JP | 2011-063588 A | 3/2011 |
| JP | 2017-88579 A | 5/2017 |

OTHER PUBLICATIONS

JPO, International Search Report issued in International Application No. PCT/JP2018/035759, dated Jan. 8, 2019.
Trefor Evans, et al., Practical Modern Hair Science, Chapter 4, Allured Business Media, ISBN: 978-1-932633-93-1, Copyright 2021.†

\* cited by examiner
† cited by third party

*Primary Examiner* — Eisa B Elhilo
(74) *Attorney, Agent, or Firm* — Lorenz & Kopf, LLP

(57) ABSTRACT

The problem of the present disclosure is to impart manageability and flexibility to hair after being dyed or bleached using an oxidative hair dye or a hair bleaching agent. The features for solving the problem are a first agent of an oxidative hair dye or a hair bleaching agent comprising: (A) a polyvalent carboxylic acid having no hydroxyl group or a salt thereof; (B) a surfactant including (B1) a cationic surfactant and (B2) a nonionic surfactant; (C) an oily component; and (D) an alkaline agent.

3 Claims, No Drawings

FIRST AGENT FOR OXIDATION HAIR DYE OR HAIR DECOLORIZING AGENT

CROSS-REFERENCE TO RELATED APPLICATION

This application is a U.S. National-Stage entry under 35 U.S.C. § 371 based on International Application No. PCT/JP2018/035759, filed Sep. 26, 2018, which was published under PCT Article 21(2) and which claims priority to Japanese Application No. 2018-068684, filed Mar. 30, 2018, which are all hereby incorporated in their entirety by reference.

TECHNICAL FIELD

The present disclosure relates to an oxidative hair dye or a hair bleaching agent. In particular, it relates to a first agent thereof.

BACKGROUND

Oxidative hair dyes or hair bleaching agents, which dye or bleach hair by oxidation reaction in the co-presence of an alkaline agent, an oxidant and the like, are widely used. An oxidative hair dye or a hair bleaching agent usually has a first agent that is a composition containing an alkaline agent, and a second agent that is a composition containing an oxidant. They are mixed immediately before use.

The first agent of the oxidative hair dye further contains an oxidation dye. When the first agent and the second agent of the oxidative hair dye are mixed, the oxidation dye is oxidized and develops color, so that hair is dyed. On the other hand, the first agent of the hair bleaching agent contains no dye. When the first agent and the second agent of the hair bleaching agent are mixed, oxygen is generated, and this oxygen decomposes the melanin in the hair to bleach the hair.

The alkaline agent and the oxidant act on hair tissue, and promote desorption of pigments and penetration of dyes. Therefore, the oxidative hair dye or the hair bleaching agent sometimes damages hair. In order to prevent hair damage and maintain a cohesive feeling and body/resilience also in the dyed hair, cationic polymers have been previously used (for example, Patent Document 1). However, it is necessary to blend a considerable amount of cationic polymers in order to obtain a sufficient effect, resulting in an increase in viscosity of the oxidative hair dye or the hair bleaching agent. Therefore, it is hardly spread during application, thus becoming difficult to be uniformly applied to the hair. Furthermore, depending on the hair type, it sometimes feels stiff or coarse.

Patent Document 2 discloses a hair cosmetic blended with succinic acid, which suppresses peeling of cuticles when hair is stretched, and can enhance finish shine and cohesiveness. It discloses a hair rinse, a hair conditioner, a hair treatment, and a hair pack as the hair cosmetic. However, no hair dye or hair bleaching agent is herein disclosed.

Hair cosmetics such as a hair rinse or hair treatment agents which are applied to hair adhere to all of the hair. On the other hand, hair dyes or hair bleaching agents are selectively applied to a portion that requires color adjustment. Both of them are hair treatment agents which differ in properties, i.e., the hair cosmetics do not require application properties enabling the application in different colors, whereas the hair dyes or hair bleaching agents require good application operability in that they are easily applied only to the hair portion required. Here, good application operability refers to a property in which it hardly drips due to its viscosity, and yet has good spreadability, therefore it is easily and uniformly applied only to a hair portion required.

BACKGROUND ART DOCUMENTS

Patent Documents

Patent Document 1: JP 2005-23023 A
Patent Document 2: JP 2017-88579 A

BRIEF SUMMARY

It is an object of the present disclosure to provide a first agent of an oxidative hair dye or a hair bleaching agent which can impart manageability and flexibility to the hair after being dyed or bleached.

First agents of an oxidative hair dye or a hair bleaching agent are provided. In an exemplary embodiment, the first agent includes (A) a polyvalent carboxylic acid having no hydroxyl groups, or a salt thereof. The first agent also includes a surfactant (B), where the surfactant includes (B1) a cationic surfactant and (B2) a nonionic surfactant. The first agent further includes an oily component and an alkaline agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure provides a first agent of an oxidative hair dye or a hair bleaching agent comprising:

(A) a polyvalent carboxylic acid having no hydroxyl group or a salt thereof;
(B) a surfactant including (B1) a cationic surfactant and (B2) a nonionic surfactant;
(C) an oily component; and
(D) an alkaline agent.

In one embodiment, the polyvalent carboxylic acid having no hydroxyl group is at least one selected from the group including succinic acid, maleic acid and fumaric acid.

One embodiment contains from about 0.01 to about 3% by weight of the polyvalent carboxylic acid having no hydroxyl group with respect to the whole first agent of the hair dye.

In one embodiment, the weight ratio of component (B) with respect to component (A) ((B)/(A)) is from about 3 to about 100.

In one embodiment, any of the first agents contain as component (C) from about 2 to about 12% by weight of a higher alcohol (C1) which is solid at ambient temperature.

Also, the present disclosure provides an oxidative hair dye or a hair bleaching agent comprising any of the first agents, and a second agent of the hair dye or the hair bleaching agent, which contains an oxidant.

Effect of Present Disclosure

According to the present disclosure, manageability and flexibility can be imparted to the hair after being dyed or bleached using the oxidative hair dye or the hair bleaching agent. Also, the first agent of the oxidative hair dye or the hair bleaching agent having excellent application operability is provided.

Embodiments for Carrying Out the Present Disclosure

Embodiments of the present disclosure will hereinafter be described by giving specific examples of the respective components. All the respective components may be used alone or in combination of two or more. Also, in the present specification, the wording "hair dye" means an oxidative hair dye or a hair bleaching agent having a first agent and a second agent.

Component (A): Polyvalent Carboxylic Acid Having No Hydroxyl Group or a Salt Thereof The polyvalent carboxylic acid is a compound having a plurality of carboxyl groups. The polyvalent carboxylic acid may be either of an aliphatic polyvalent carboxylic acid, an alicyclic polyvalent carboxylic acid, and an aromatic polyvalent carboxylic acid. The polyvalent carboxylic acid is a compound substantially having a specific molecular weight, and polymers are not included therein. The polyvalent carboxylic acid has no hydroxyl group. When the polyvalent carboxylic acid having a hydroxyl group is used, manageability and flexibility of hair, and application operability are insufficient. The polyvalent carboxylic acid has 2 to 16, preferably 2 to 10, and more preferably 3 to 6 carbon atoms.

Examples of the polyvalent carboxylic acid used herein include, for example, oxalic acid, malonic acid, succinic acid, glutaric acid, adipic acid, trimethyl adipic acid, pimelic acid, 2,2-dimethylglutaric acid, azelaic acid, sebacic acid, fumaric acid, maleic acid, itaconic acid, dodecanedioic acid, glutaric acid, 1,3-cyclopentane dicarboxylic acid, 1,2-cyclohexane dicarboxylic acid, 1,3-cyclohexane dicarboxylic acid, 1,4-cyclohexane dicarboxylic acid, phthalic acid, terephthalic acid, isophthalic acid, 2,5-norbornane dicarboxylic acid, 1,4-naphthalic acid, diphenic acid, 4,4'-oxydibenzoic acid, diglycolic acid, thiodipropionic acid, 4,4'-sulfonyldibenzoic acid, 2,5-naphthalene dicarboxylic acid, 2,6-naphthalene dicarboxylic acid and the like. One or two or more of them may be used alone or in combination. Among them, succinic acid, maleic acid, and fumaric acid are preferred. The particularly preferred polyvalent carboxylic acid is succinic acid.

Examples of the cationic component which constitutes a salt of the polyvalent carboxylic acid include, for example, alkali metals such as sodium and potassium; alkanol amine derived cations such as ammonium, monoethanolamine, diethanolamine and triethanolamine; and basic amino acid derived cations such as alginine and lysine.

The polyvalent carboxylic acid or salt thereof of component (A) is blended as an acid in an amount of from about 0.01 to about 3% by weight with respect to the whole first agent of the hair dye. Adjustment of the blending amount of the polyvalent carboxylic acid within the above range improves manageability and flexibility of the hair after being dyed or bleached, and also improves application operability. The blending amount of the polyvalent carboxylic acid is preferably from about 0.1 to about 2% by weight, more preferably from about 0.3 to about 1.5% by weight.

Component (B): Surfactant

In the present disclosure, for improving feel of hair and stability, a cationic surfactant (B1) and a nonionic surfactant (B2) are used in combination as surfactants of component (B).

Examples of the cationic surfactant of component (B1) include lauryl trimethyl ammonium chloride, stearyl trimethyl ammonium chloride, cetyl trimethyl ammonium chloride, behenyl trimethyl ammonium chloride, distearyl dimethyl ammonium chloride, cetyl trimethyl ammonium bromide, stearyl trimethyl ammonium bromide, benzalkonium chloride, tri(polyoxyethylene) stearyl ammonium chloride and the like. Preferably lauryl trimethyl ammonium chloride, stearyl trimethyl ammonium chloride, cetyl trimethyl ammonium chloride, behenyl trimethyl ammonium chloride, cetyl trimethyl ammonium bromide, stearyl trimethyl ammonium bromide, and more preferably stearyl trimethyl ammonium chloride, and cetyl trimethyl ammonium chloride are used in terms of the stability of the agent and a finished feel. These cationic surfactants may be used alone or in combination of two or more.

Examples of the nonionic surfactant of component (B2) include polyoxyethylene (hereinafter referred to as POE) alkyl ethers, POE alkyl phenyl ethers, POE-polyoxypropylene (hereinafter referred to as POP) alkyl ethers, POE sorbitan fatty acid esters, POE propylene glycol fatty acid esters and the like. Among them, POE alkyl ethers, POE alkyl phenyl ethers, POE-POP alkyl ethers, and POE sorbitan fatty acid esters are preferred since they remain unaltered by the addition of an acid or an alkali, and POE alkyl ethers are more preferred. Specific examples of the POE alkyl ethers include POE lauryl ether, POE cetyl ether, POE cetostearyl ether, POE stearyl ether, POE behenyl ether and the like. These nonionic surfactants may be used alone or in combination of two or more.

The weight ratio (B2)/(B1) in component (B) is perceived to be from about 1 to about 10, preferably from about 2 to about 7, and more preferably from about 3 to about 6, in order to obtain a viscosity with excellent coating properties. The total content of component (B) is perceived to be from about 1 to about 15% by weight in the first agent of the hair dye of the present disclosure, preferably from about 2 to about 12% by weight, and more preferably from about 4 to about 10% by weight, in terms of the stability of the composition. The weight ratio of (B)/(A) is perceived to be from about 3 to about 100, preferably from about 5 to about 50, in terms of the stability of the composition.

Component (C): Oily Component

The oily component of component (C) is blended in order to improve the stability and gives moisture to the finished hair. Examples of the oily component include those which are liquid (CL) and those which are solid (CS) (including paste-like) depending on the characteristics at ambient temperature. Oily components (CS) which are solid at ambient temperature include a higher alcohol (C1).

In the present disclosure, in terms of the preservation stability and the viscosity adjustment, the higher alcohol (C1), which is at least solid at ambient temperature, is used preferably in an amount ranging from about 2 to about 12% by weight in the first agent of the hair dye of the present disclosure, more preferably from about 3 to about 10% by weight, and even more preferably from about 4 to about 8% by weight.

Examples of the higher alcohol of component (C1) include myristyl alcohol, cetyl alcohol, stearyl alcohol, cetostearyl alcohol, aralkyl alcohol, behenyl alcohol, lanolin alcohol and the like. They may be used alone or in combination of two or more.

Among the oily components of component (C), examples of those which are liquid (CL) at ambient temperature include hydrocarbon oils, animal fats and vegetable oils, higher alcohols, higher fatty acids, ester oils, silicone oils and the like. Examples of the hydrocarbon oils include α-olefin oligomer, light isoparaffin, light liquid isoparaffin, squalane, polybutene, liquid isoparaffin, liquid paraffin and the like. Examples of the animal fats and vegetable oils include olive oil, camellia oil, tea oil, sasanqua oil, safflower oil, sunflower oil, soybean oil, cotton oil, sesame oil, corn oil, peanut oil, rapeseed oil, rice bran oil, rice germ oil, wheat germ oil, coix lacryma-jobi ma-yuan seed oil, grape seed oil, almond oil, avocado oil, carrot oil, macadamia nut oil, castor oil, linseed oil, palm oil, mink oil, egg-yolk oil, jojoba oil and the like. Examples of the higher alcohols include isostearyl alcohol, 2-octyldodecanol, decyltetradecanol, oleyl alcohol, 2-hexyldecanol, linoleyl alcohol, linolenyl alcohol and the like. Examples of the higher fatty acids include isostearic acid, oleic acid, linoleic acid and the like. Examples of the ester oils include diisopropyl adipate, diisobutyl adipate, dioctyl adipate, di(2-hexyldecyl) adipate, diisostearyl adipate, isostearyl myristate, isotridecyl myristate, isopropyl myristate, octyldodecyl myristate, cetyl octanoate, isononyl isononanoate, isodecyl isononanoate, isotridecyl isononanoate, diisopropyl cebacate, isopropyl palmitate, hexyl laurate, decyl oleate, hexyldecyl dimethyl octanoate, octyl palmitate, lauryl lactate, octyldodecyl lactate, isocetyl stearate, isocetyl isostearate, ethylene glycol dioctanoate, dipentaerythritol fatty acid ester, cetyl caprylate, glyceryl tricaprylate, neopentyl glycol dicaprylate, diisostearyl malate, dioctyl succinate and the like. Examples of the silicone oils include methyl polysiloxane, methyl phenyl polysiloxane, methyl cyclopolysiloxane, polyether-modified silicone, betaine-modified silicone, alkyl-modified silicone, alkoxy-modified silicone and the like.

Among the oily components of component (C), examples of those which are solid (CS) at ambient temperature other than those of component (C1) include hydrocarbons, animal fats, waxes, higher fatty acids, esters and the like. Examples of the hydrocarbons include ozokerite, cerecin, paraffin, polyethylene powder, microcrystalline wax, Vaseline® (petroleum jelly) and the like. Examples of the animal fats include beef tallow, cacao butter and the like. Examples of the waxes include bees wax, candelilla wax, carnauba wax, lanolin and the like. Examples of the higher fatty acids include lauric acid, myristic acid, palmitic acid, stearic acid, behenic acid, hydroxystearic acid, undecylenic acid, ricinoreic acid and the like. Examples of the esters include butyl stearate, stearyl stearate, cetyl myristate, myristyl myristate, cetyl palmitate, cetyl lactate, myristyl lactate, lanolin acetate, cholesteryl stearate, cholesteryl oleate and the like.

The total content of component (C) as the oily component is perceived to be from about 2 to about 20% by weight in the first agent of the hair dye of the present disclosure, preferably from about 5 to about 15% by weight, particularly from about 8 to about 13% by weight in order to obtain adequate viscosity. Furthermore, in the oily component of component (C), the weight ratio of the whole component (C) with respect to the higher alcohol (C1), which is solid at ambient temperature, i.e., (C)/(C1), is from about 1.1 to about 3, particularly preferably from about 1.5 to about 2 in terms of the operability and the preservation stability. The weight ratio of (C)/(A) is perceived to be from about 5 to about 100 in terms of the stability of the composition, preferably from about 8 to about 50.

Component (D): Alkaline Agent

The alkaline agent of component (D) is blended in order to swell hair, penetrate a dye into the hair, and improve hair bleaching power. Examples of the alkaline agent include ammonia; alkanolamines such as monoethanolamine, isopropanolamine, 2-amino-2-methylpropanol, and 2-aminobutanol; alkanediamines such as 1,3-propanediamine; and inorganic bases such as sodium hydroxide, and potassium hydroxide.

Of the above alkaline agents, ammonia and an alkanolamine are preferred. As the alkanolamine, monoethanolamine is preferred. Furthermore, their salts are preferably used in combination, and particularly preferably ammonium carbonate, ammonium hydrogen carbonate, and ammonium chloride.

Two or more of these alkaline agents may be used in combination. The content thereof is preferably from about 0.05 to about 15% by weight in the first agent of the present disclosure, more preferably from about 0.1 to about 10% by weight, and particularly from about 0.2 to about 8% by weight in terms of sufficient bleaching and dyeing effects and reduction of hair damage and scalp irritation.

Component (E): Hair Protective Agent

A hair protective agent of component (E) is blended as necessary in order to improve foaming during shampooing, smoothness of hair, cohesiveness during drying and moisture-retaining properties. The hair protective agent includes a cationic polymer (E1) and an amino-modified silicone (E2).

The cationic polymer of component (E1) refers to a polymer having a cation group or a group which can be ionized to a cation group, and also includes amphoteric polymers which become cationic as a whole. That is, examples of the cationic polymer include polymers in the form of an aqueous solution which contain, at a side chain of the polymer chain, an amino group or an ammonium group, or a diallyl quaternary ammonium salt as a constituent unit, such as cationic cellulose derivatives, cationic starches, cationic guar gum derivatives, polymers or copolymers of a diallyl quaternary ammonium salt, and quaternized polyvinylpyrrolidone derivatives. Among them, polymers containing a diallyl quaternary ammonium salt as a constituent unit, quaternized polyvinylpyrrolidone derivatives, and cationic cellulose derivatives are preferred in terms of the effects of softness, smoothness and ease of running fingers through hair particularly during shampooing, manageability of hair and moisture retention during drying, as well as the stability of the composition. Polymers or copolymers of a diallyl quaternary ammonium salt and cationic cellulose derivatives are more preferred, and polymers or copolymers of a diallyl quaternary ammonium salt are most preferred.

The amino-modified silicone as component (E2) may be any amino-modified silicone as long as it has an amino group, an imino group or an ammonium group. Examples thereof include, for example, aminopropyl methyl siloxane-dimethylsiloxane copolymer (aminopropyl dimethicone), aminoethyl aminopropyl siloxane-dimethylsiloxane copolymer (amodimethicone), and aminoethyl aminopropyl methyl siloxane-dimethylsiloxane copolymer (trimethylsilylamodimethicone).

The content of component (E) is from about 0.1 to about 5% by weight in the first agent of the hair dye of the present disclosure, particularly preferably from about 0.2 to about 3% by weight.

Component (F): Oxidation Dye Intermediate or Direct Dye

When the present disclosure is a hair bleaching agent, the first agent does not contain component (F), whereas when it is an oxidative hair dye, the first agent of the hair dye contains component (F).

As oxidation dye intermediates, publicly known precursors and couplers which are commonly used for hair dyes may be used. Examples of the precursors include, for example, paraphenylenediamine, toluene-2,5-diamine, 2-chloro-paraphenylenediamine, N-methoxyethyl-paraphenylenediamine, N,N-bis(2-hydroxyethyl)-paraphenylenediamine, 2-(2-hydroxyethyl)-paraphenylenediamine, 2,6-dimethyl-paraphenylenediamine, 4,4'-diaminodiphenylamine, 1,3-bis(N-(2-hydroxyethyl)-N-(4-aminophenyl)amino)-2-propanol, PEG-3,3,2'-paraphenylenediamine, paraaminophenol, orthoaminophenol, paramethyl aminophenol, 3-methyl-4-aminophenol, 2-aminomethyl-4-aminophenol, 2-(2-hydroxyethylaminomethyl)-4-aminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraaminopyrimidine, 2,5,6-triamino-4-hydroxypyrimidine, 4,5-diamino-1-(4'-chlorobenzyl)pyrazole, 4,5-diamino-1-hydroxyethyl pyrazole, salts thereof and the like.

Examples of the couplers include, for example, methphenylenediamine, 2,4-diaminophenoxyethanol, 2-amino-4-(2-hydroxyethylamino)anisole, 2,4-diamino-5-methylphenetol, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, methaminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-methaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, 2,6-diaminopyridine and salts thereof, and the like.

Two or more of the precursors and the couplers may be used in combination, and their contents are each from about 0.01 to about 8% by weight in the first agent of the hair dye of the present disclosure, particularly preferably from about 0.1 to about 5% by weight.

Examples of the direct dye include a nitro dye, a dispersion dye, a basic dye and the like. Examples of the nitro dye include 2-nitro-paraphenylenediamine, 2-amino-6-chloro-4-nitrophenol, 3-nitro-parahydroxyethylaminophenol, 4-nitro-orthphenylenediamine, 4-amino-3-nitrophenol, 4-hydroxypropylamino-3-nitrophenol, HC Blue No. 2, HC Orange No. 1, HC Red No. 1, HC Yellow No. 2, HC Yellow No. 4, HC Yellow No. 5, HC Red No. 3, N,N-bis-(2-hydroxyethyl)-2-nitro-paraphenylenediamine and the like. Examples of the dispersion dye include Disperse Violet 1, Disperse Blue 1, Disperse Black 9 and the like. Examples of the basic dye include Basic Blue 99, Basic Brown 16, Basic Brown 17, Basic Red 76, Basic Red 51, Basic Yellow 57, Basic Yellow 87, Basic Orange 31 and the like.

Two or more of the direct dye may be used in combination, and the direct dye may also be used in combination with the oxidation dye intermediate. The content thereof is from about 0.001 to about 5% by weight in the first agent of the hair dye of the present disclosure, particularly preferably from about 0.01 to about 3% by weight.

Other Components

Other than the above respective components, as necessary, various additives, which are blended in usual cosmetics, may be blended in the first agent of the hair dye as long as they do not impair the function of the first agent of the hair dye. Examples of such additives include, for example, a solvent, an antioxidant, a pH adjuster, a chelating agent, a preservative, a perfume and the like.

The pH (25° C.) of the first agent of the hair dye of the present disclosure is from about 8 to about 12, particularly preferably from about 9 to about 11. Examples of the pH adjuster other than the above alkaline agents include inorganic acids such as hydrochloric acid, and phosphoric acid; organic acids such as citric acid, glycolic acid, and lactic acid; inorganic acid salts or organic acid salts such as potassium dihydrogen phosphate, disodium hydrogen phosphate, and sodium citrate; carbonates such as guanidine carbonate, sodium carbonate, potassium carbonate, sodium hydrogen carbonate, and potassium hydrogen carbonate.

Second Agent of Hair Dye

As the second agent of the hair dye, a publicly known second agent used in the field of hair dyes is used. The second agent includes a publicly known oxidant used in the field of hair dyes.

The oxidant is not particularly limited, and examples thereof include, for example, hydrogen peroxide, sodium perborate, potassium perborate, sodium percarbonate, sodium bromate and the like. Among them, hydrogen peroxide is particularly preferred since sufficient dyeing power and bleaching power are obtained. These oxidants may be contained alone or may be contained in combination of two or more.

The content of the oxidant is set as needed depending on the amount which can oxidize all of the oxidation dye, the desired bleaching power and the like. Although not particularly limited, it is preferably about 0.01% by weight or more with respect to the total weight of the first agent and the second agent, more preferably about 0.1% by weight or more, in order to obtain sufficient dyeing power and bleaching power. Furthermore, even if it is contained in an amount exceeding about 15% by weight with respect to the total weight of the first agent and the second agent, more dyeing power is not obtained. Therefore, the content is preferably not more than about 15% by weight, more preferably not more than about 10% by weight.

Antioxidant, Metal Sequestering Agent

The hair dye of the present disclosure may contain an antioxidant in order to inhibit development of color due to oxidation of the hair dye before being mixed and used. Examples of the antioxidant include, for example, thioglycolic acid, calcium thioglycolate, ammonium thioglycolate, sodium sulfite, ascorbic acid, sodium ascorbate, ammonium ascorbate, propyl gallate, tocopherol, L-cysteine, homocysteine, N-acetyl-L-cysteine and the like. Further, in order to inhibit influence of metal ions as impurities, it may contain a metal sequestering agent. Examples of the metal sequestering agent include, for example, edetic acid, disodium edetate, tetrasodium edetate, sodium metaphosphate, sodium polyphosphate and the like.

Solvent

The hair dye of the present disclosure may contain a solvent in order to improve the solubility of the dye. Examples of the solvent include low molecular weight alcohols such as ethanol, and isopropyl alcohol.

Preparation Method

The hair dye of the present disclosure may be prepared by a publicly known method. For example, the first agent and the second agent can be prepared by dissolving or mixing the above-described components with water, mixing and stirring them after warming a part of them as necessary, cooling them, adding the remaining components, and stirring and mixing them. Usually, purified water is used. The water content is the remainder when the respective components are contained in predetermined amounts, it is preferably about 10% by weight or more and not more than about 95% by weight with respect to the total weight of each individual first agent or second agent, and it is adjusted as needed depending on the kind, content and the like of each component.

Usage

The hair dye of the present disclosure can be used for dyeing hair by a publicly known method in which, for example, the first agent and the second agent are mixed immediately before use, the mixture is applied to hair and the like. The hair dyeing time is adjusted as needed depending on the type and amount of the oxidation dye, the amount of application to hair, and the desired dyeing degree. It is about 5 minutes or more, preferably from about 5 to about 50 minutes, and more preferably from about 10 to about 45 minutes.

The hair dye of the present disclosure can be prepared in dosage forms such as cream, liquid, gel-like and foam-like as long as they do not spoil the effects of the present disclosure, but it is not limited to these dosage forms. Furthermore, the first agent and the second agent may have mutually different forms in which the first agent is cream and the second agent is liquid. The mixing ratio of the first agent and the second agent is also indifferent.

EXAMPLES

The present disclosure will more specifically be described by the following Examples. However, it should not be construed that the disclosure of the present application is limited by them. The blended amounts of the components shown in the Examples are indicated by the unit of parts by weight unless otherwise indicated.

Examples 1 to 9 and Comparative Examples 1 to 10

Production of Second Agent of Hair Dye

A second agent of a hair dye was produced by uniformly mixing components in predetermined amounts shown in Table 1 using a mixing stirrer.

TABLE 1

| Component | Blended Amount |
|---|---|
| Hydrogen peroxide solution (35%) | 17 |
| Cetanol | 5 |
| Polyoxyethylene cetostearyl ether 30 EO | 0.5 |
| Lipophilic glycerol monostearate | 0.5 |
| Liquid paraffin | 0.5 |
| Propylene glycol | 0.5 |
| Coconut oil fatty acid amidopropyl betaine solution (30%) | 0.5 |
| Sodium benzoate | 0.1 |
| Hydroxyethane diphosphonic acid solution (60%) | 0.3 |
| Phenoxy ethanol | 0.3 |
| Sodium hydrogen phosphate | Appropriate amount |
| Purified water | The remainder |
| Total | 100 |

Production of First Agent of Hair Dye

First agents of hair dyes of Examples 1 to 9 and Comparative Examples 1 to 10 were produced by uniformly mixing components in predetermined amounts shown in Tables 2 to 4.

In the tables, "EO" means an ethylene oxide adduct, and the numerical value before that indicates the addition number of EO. "EDTA-4Na" means tetrasodium edetate.

Performance Evaluation of Hair Dye

Using the first agents and second agent of the hair dyes thus produced, the following performance evaluation was conducted. The evaluation results are shown in Tables 2 to 4.

(1) Emulsified State

A mixed state of the first agent was observed by visual check, and judged on a four-point scale of excellent (⊚), good (○), somewhat poor (Δ), and poor (X). When it is evaluated as somewhat poor (Δ) or poor (X) in terms of the emulsified state, subsequent evaluation is not conducted, and evaluated as (X).

(2) Preservation Stability

The first agent was preserved at about 40° C. for about 6 months in a glass container. Then, a change in its appearance was observed, and evaluated on a four-point scale of excellent: no change (⊚), good (○), somewhat poor: decrease in viscosity (Δ), and poor: separation (X).

(3) Application Operability

When a hair dye in which the first agent and the second agent were mixed in equal amounts was applied to a human head using a brush, a sensory evaluation in terms of the application operability such as dripping or application irregularities was conducted, and evaluated on a four-point scale of excellent (⊚), good (○), somewhat poor (Δ), and poor (X). (Excellent: Viscous cream with good spreadability and no drips, which can be evenly applied.)

(4) Flexibility

A hair dye in which the first agent and the second agent were mixed in equal amounts was applied to a human head using a brush, and it was washed out after left to stand for about 30 minutes. The head was dried with a dryer after shampooing and conditioner treatment. The flexibility of the hair was evaluated. The evaluation was conducted on a four-point scale of excellent (◎), good (○), somewhat poor (Δ), and poor (X) by five specialized panelists. (Excellent: Hair has elasticity, and a supple finish is obtained.)

(5) Feel and Smoothness of Hair

A sensory evaluation on a feel when the hair after the hair-dyeing treatment was touched with fingers was conducted on a four-point scale of excellent (◎), good (○), somewhat poor (Δ), and poor (X).

(6) Cohesive Feeling of Hair

A sensory evaluation on a cohesive feeling of the hair after the hair-dyeing treatment was conducted on a four-point scale of excellent (◎), good (○), somewhat poor (Δ), and poor (X). (Excellent: Hair does not get dried out, and a cohesive finish is obtained.)

(7) Hair-Dyeing Power and Dyeing Levelness

A dyeing degree and a color irregularity of the hair after the hair-dyeing treatment was visually observed, and evaluated on a four-point scale of excellent (◎), good (○), somewhat poor (Δ) and poor (X).

TABLE 2

| | Component | Example 1 | Example 2 | Example 3 | Example 4 | Example 5 | Example 6 | Example 7 |
|---|---|---|---|---|---|---|---|---|
| Blended amount | Cetostearyl alcohol | 6 | 6 | 5 | 7.5 | 6 | 6 | 6 |
| | Liquid paraffin | 4 | 4 | 3 | 4.7 | 4 | 4 | 4 |
| | Polyoxyethylene cetostearyl ether 30 EO | 3 | 3 | 3 | 5 | 3 | 3 | 3 |
| | Polyoxyethylene cetostearyl ether 6 EO | 1 | 1 | 1 | 1.2 | 1 | 1 | 1 |
| | Polyoxyethylene stearyl ether 100 EO | 2.5 | 2.5 | 2.5 | 3 | 2.5 | 2.5 | 2.5 |
| | Trimethylstearylammonium chloride (80%) | 2 | 2 | 2 | 2 | 2 | 2 | 2 |
| | Glycerin | 4 | 4 | 4 | 4 | 4 | 4 | 4 |
| | Propylene glycol | 4 | 4 | 4 | 4 | 4 | 4 | 4 |
| | EDTA-4Na | 0.2 | 0.2 | 0.2 | 0.2 | 0.2 | 0.2 | 0.2 |
| | Sodium sulfite | 0.4 | 0.4 | 0.4 | 0.4 | 0.4 | 0.4 | 0.4 |
| | Ascorbic acid | 0.2 | 0.2 | 0.2 | 0.2 | 0.2 | 0.2 | 0.2 |
| | Ammonia water (28%) | 5 | 5 | 5 | 5 | 5 | 5 | 5 |
| | Ammonium hydrogen carbonate | 1 | 1 | 1 | 1 | 1 | 1 | 1 |
| | Aminoethylaminopropylmethyl siloxane-dimethylsiloxane copolymer | 0.5 | 0.5 | 0.5 | 0.5 | 0.5 | 1 | 0.1 |
| | Dimethyldiallylammonium chloride-acrylic acid copolymer solution (38%) | 0.5 | 0.5 | 0.5 | 0.5 | 0.5 | 1 | 0.1 |
| | Perfume | 0.2 | 0.2 | 0.2 | 0.2 | 0.2 | 0.2 | 0.2 |
| | Sulfuric acid toluene-2,5-diamine | 1 | 1 | 1 | 1 | 1 | 1 | 1 |
| | Resorcin | 0.5 | 0.5 | 0.5 | 0.5 | 0.5 | 0.5 | 0.5 |
| | Succinic acid | 0.7 | | 0.7 | 1.5 | 0.3 | 0.7 | 0.7 |
| | Sodium succinate | | 1 | | | | | |
| | Potassium hydroxide | 0.6 | 0.6 | 0.6 | 0.6 | 0.6 | 0.6 | 0.6 |
| | Amino methyl propanol | 0.3 | 0.3 | 0.3 | 0.3 | 0.3 | 0.3 | 0.3 |
| | Purified water | The remainder | The remainder | The remainder | The remainder | The remainder | The remainder | The remainder |
| | Total | 100 | 100 | 100 | 100 | 100 | 100 | 100 |
| Evaluation results | (1) Emulsified state | ◎ | ○ | ◎ | ○ | ◎ | ◎ | ◎ |
| | (2) Preservation stability | ◎ | ◎ | ◎ | ◎ | ◎ | ◎ | ◎ |
| | (3) Application operability | ◎ | ◎ | ○ | ○ | ○ | ◎ | ◎ |
| | (4) Flexibility | ◎ | ◎ | ◎ | ◎ | ○ | ○ | ◎ |
| | (5) Feel/smoothness of hair | ◎ | ◎ | ◎ | ◎ | ◎ | ◎ | ○ |
| | (6) Cohesive feeling of hair | ◎ | ◎ | ◎ | ◎ | ○ | ◎ | ◎ |
| | (7) Hair-dyeing power and dyeing levelness | ◎ | ◎ | ◎ | ◎ | ◎ | ◎ | ◎ |

TABLE 3

| | Component | Example 8 | Example 9 | Comp. Ex. 1 | Comp. Ex. 2 | Comp. Ex. 3 | Comp. Ex. 4 | Comp. Ex. 5 |
|---|---|---|---|---|---|---|---|---|
| Blended amount | Cetostearyl alcohol | 6 | 6 | 6 | 6 | | 6 | 6 |
| | Liquid paraffin | 4 | 4 | 4 | 4 | 4 | | 4 |
| | Polyoxyethylene cetostearyl ether 30 EO | 3 | 3 | 3 | 3 | 3 | 3 | |
| | Polyoxyethylene cetostearyl ether 6 EO | 1 | 1 | 1 | 1 | 1 | 1 | |

TABLE 3-continued

| Component | Example 8 | Example 9 | Comp. Ex. 1 | Comp. Ex. 2 | Comp. Ex. 3 | Comp. Ex. 4 | Comp. Ex. 5 |
|---|---|---|---|---|---|---|---|
| Polyoxyethylene stearyl ether 100 EO | 2.5 | 2.5 | 2.5 | 2.5 | 2.5 | 2.5 | |
| Trimethylstearylammonium chloride (80%) | 2 | 2 | 2 | 2 | 2 | 2 | 2 |
| Glycerin | 4 | 4 | 4 | 4 | 4 | 4 | 4 |
| Propylene glycol | 4 | 4 | 4 | 4 | 4 | 4 | 4 |
| EDTA-4Na | 0.2 | 0.2 | 0.2 | 0.2 | 0.2 | 0.2 | 0.2 |
| Sodium sulfite | 0.4 | 0.4 | 0.4 | 0.4 | 0.4 | 0.4 | 0.4 |
| Ascorbic acid | 0.2 | 0.2 | 0.2 | 0.2 | 0.2 | 0.2 | 0.2 |
| Ammonia water (28%) | 5 | 5 | 5 | 5 | 5 | 5 | 5 |
| Ammonium hydrogen carbonate | 1 | 1 | 1 | 1 | 1 | 1 | 1 |
| Aminoethylaminopropylmethyl siloxane-dimethylsiloxane copolymer | 1 | | 0.5 | 0.5 | 0.5 | 0.5 | 0.5 |
| Dimethyldiallylammonium chloride-acrylic acid copolymer solution (38%) | | 1 | 0.5 | 0.5 | 0.5 | 0.5 | 0.5 |
| Perfume | 0.2 | 0.2 | 0.2 | 0.2 | 0.2 | 0.2 | 0.2 |
| Sulfuric acid toluene-2,5-diamine | 1 | 1 | 1 | 1 | 1 | 1 | 1 |
| Resorcin | 0.5 | 0.5 | 0.5 | 0.5 | 0.5 | 0.5 | 0.5 |
| Succinic acid | 0.7 | 0.7 | | 3.5 | 0.7 | 0.7 | 0.7 |
| Sodium succinate | | | | | | | |
| Potassium hydroxide | 0.6 | 0.6 | 0.6 | 0.6 | 0.6 | 0.6 | 0.6 |
| Amino methyl propanol | 0.3 | 0.3 | 0.3 | 0.3 | 0.3 | 0.3 | 0.3 |
| Purified water | The remainder | The remainder | The remainder | The remainder | The remainder | The remainder | The remainder |
| Total | 100 | 100 | 100 | 100 | 100 | 100 | 100 |
| Evaluation results (1) Emulsified state | ◎ | ◎ | ◎ | △ | X | X | X |
| (2) Preservation stability | ◎ | ◎ | ◎ | X | X | X | X |
| (3) Application operability | ◎ | ◎ | △ | X | X | X | X |
| (4) Flexibility | ◎ | ◎ | △ | X | X | X | X |
| (5) Feel and smoothness of hair | ○ | ○ | ○ | X | X | X | X |
| (6) Cohesive feeling of hair | ◎ | ◎ | △ | X | X | X | X |
| (7) Hair-dyeing power and dyeing levelness | ◎ | ◎ | ○ | X | X | X | X |

TABLE 4

| | Component | Comp. Ex. 6 | Comp. Ex. 7 | Comp. Ex. 8 | Comp. Ex. 9 | Comp. Ex. 10 |
|---|---|---|---|---|---|---|
| Blended amount | Cetostearyl alcohol | 6 | 6 | 6 | 6 | 6 |
| | Liquid paraffin | 4 | 4 | 4 | 4 | 4 |
| | Polyoxyethylene cetostearyl ether 30EO | 6 | 3 | 3 | 3 | 3 |
| | Polyoxyethylene cetostearyl ether 6EO | 2 | 1 | 1 | 1 | 1 |
| | Polyoxyethylene stearyl ether 100EO | 6 | 2.5 | 2.5 | 2.5 | 2.5 |
| | Trimethylstearylammonium chloride (80%) | 2 | 2 | 2 | 2 | 2 |
| | Glycerin | 4 | 4 | 4 | 4 | 4 |
| | Propylene glycol | 4 | 4 | 4 | 4 | 4 |
| | EDTA-4Na | 0.2 | 0.2 | 0.2 | 0.2 | 0.2 |
| | Sodium sulfite | 0.4 | 0.4 | 0.4 | 0.4 | 0.4 |
| | Ascorbic acid | 0.2 | 0.2 | 0.2 | 0.2 | 0.2 |
| | Ammonia water (28%) | 5 | 5 | 5 | 5 | 5 |
| | Ammonium hydrogen carbonate | 1 | 1 | 1 | 1 | 1 |
| | Aminoethylaminopropylmethyl siloxane-dimethylsiloxane copolymer | 0.5 | 0.5 | | 0.5 | 0.5 |
| | Dimethyldiallylammonium chloride-acrylic acid copolymer solution (38%) | 0.5 | 0.5 | | 0.5 | 0.5 |
| | Perfume | 0.2 | 0.2 | 0.2 | 0.2 | 0.2 |
| | Sulfuric acid toluene-2,5-diamine | 1 | 1 | 1 | 1 | 1 |
| | Resorcin | 0.5 | 0.5 | 0.5 | 0.5 | 0.5 |
| | Succinic acid | 0.7 | 0.7 | 0.7 | | |
| | Sodium succinate | | | | | |
| | Malic Acid | | | | 1.5 | |
| | Trisodium citrate | | | | | 3.3 |
| | Potassium hydroxide | 0.6 | 0.6 | 0.6 | 0.6 | 0.6 |
| | Amino methyl propanol | 0.3 | 0.3 | 0.6 | 0.6 | 0.6 |
| | Purified water | The remainder | The remainder | The remainder | The remainder | The remainder |
| | Total | 100 | 100 | 100 | 100 | 100 |
| Evaluation results | (1) Emulsified state | △ | △ | ◎ | ○ | ○ |
| | (2) Preservation stability | X | X | ○ | ○ | ○ |
| | (3) Application operability | X | X | △ | △ | △ |
| | (4) Flexibility | X | X | △ | △ | △ |

TABLE 4-continued

| Component | Comp. Ex. 6 | Comp. Ex. 7 | Comp. Ex. 8 | Comp. Ex. 9 | Comp. Ex. 10 |
|---|---|---|---|---|---|
| (5) Feel/smoothness of hair | X | X | Δ | ◯ | ◯ |
| (6) Cohesive feeling of hair | X | X | Δ | Δ | Δ |
| (7) Hair-dyeing power and dyeing levelness | X | X | Δ | Δ | Δ |

Reference Examples 1 and 2

Production of Hair Treatment Agent Using Succinic Acid

Hair treatment agents were produced by uniformly mixing components in predetermined amounts shown in Table 5. Reference Example 1 is a formulation corresponding to the hair cosmetic described as Example 5 in Patent Document 2. Reference Example 2 is a formulation in which the alkaline agent, the antioxidant and the like in the same amounts as those described in Table 2 of Example 1 were added to the formulation of Reference Example 1 to prepare a first agent of the hair dye.

Performance Evaluation of Hair Treatment Agent

The performance evaluation was conducted in the same manner as in the Examples except for using the hair treatment agents thus prepared. The evaluation results are shown in Table 5.

TABLE 5

| | Component | Ref. Example 1 | Ref. Example 2 |
|---|---|---|---|
| Blended amount | Succinic acid | 1.2 | 1.2 |
| | Lysine hydrochloride | 0.2 | 0.2 |
| | Behentrimonium chloride | 2 | 2 |
| | Stearyl alcohol | 5.4 | 5.4 |
| | Dipropylene alcohol | 3 | 3 |
| | Lactic acid | Adequate amount | Adequate amount |
| | Sodium hydroxide | Adequate amount | Adequate amount |
| | Water | The remainder | The remainder |
| | EDTA-4Na | | 0.2 |
| | Sodium sulfite | | 0.4 |
| | Ascorbic acid | | 0.2 |
| | Ammonia water (28%) | | 5 |
| | Ammonium hydrogen carbonate | | 1 |
| | Aminoethylaminopropylmethyl siloxane-dimethylsiloxane copolymer | | 0.5 |
| | Dimethyldiallylammonium chloride-acrylic acid copolymer solution (38%) | | 0.5 |
| | Perfume | | 0.2 |
| | Sulfuric acid toluene-2,5-diamine | | 1 |
| | Resorcin | | 0.5 |
| | Potassium hydroxide | | 0.6 |
| | Amino methyl propanol | | 0.3 |
| | Total | 100 | 100 |
| Evaluation Results | (1) Emulsified state | ◯ | X |
| | (2) Preservation stability | ⊚ | X |
| | (3) Application operability | Δ | X |
| | (4) Flexibility | ⊚ | X |
| | (5) Feel/smoothness of hair | ⊚ | X |
| | (6) Cohesive feeling of hair | Δ | X |
| | (7) Hair dyeing power and dyeing levelness | — | X |

Since the hair cosmetic of Reference Example 1 has no hair-dyeing properties, evaluation on the hair-dyeing power was not conducted. Since the hair cosmetic of Reference Example 1 was a somewhat hard cream and its spreadability was not so good, the application operability was "Δ".

The first agent of the hair dye of Reference Example 2 was unable to be emulsified, so that uniform cream was not formed. Since the evaluation from (3) Application Operability onward is unable to be conducted, it is evaluated as "X".

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A first agent of an oxidative hair dye or a hair bleaching agent comprising:
    (A) a polyvalent carboxylic acid having no hydroxyl group or a salt of the polyvalent carboxylic acid having no hydroxyl group;
    (B) a surfactant comprising (B1) a cationic surfactant and (B2) a nonionic surfactant, wherein the cationic surfactant (B1) is selected from the group of lauryl trimethyl ammonium chloride, stearyl trimethylammonium chloride, cetyl trimethylammonium chloride, behenyl trimethyl ammonium chloride, distearyl trimethyl ammonium chloride, cetyl trimethyl ammonium bromide, stearyl trimethyl ammonium chloride bromide, benzalkonium chloride, tri (polyoxyethylene) stearyl ammonium chloride, and combinations thereof; and the nonionic surfactant (B2) is selected from the group of polyoxyethylene (POE) alkyl ethers, POE alkyl phenyl ethers, POE polyoxypropylene alkyl ethers, POE sorbitan fatty acid esters, POE propylene glycol fatty acid esters, and combinations thereof;

(C) an oily component; and
(D) an alkaline agent, wherein the first agent comprises from 5 to 7.5 weight percent cetostearyl alcohol; from 3 to 4.7 weight percent liquid paraffin; from 3 to 5 weight percent polyoxyethylene cetostearyl ether with about 30 ethylene oxide adducts; from 1 to 1.2 weight percent polyoxyethylene cetostearyl ether with about 6 ethylene oxide adducts; from 2.5 to 3 weight percent polyoxyethylene stearyl ether with 100 ethylene oxide adducts; about 1.6 weight percent of trimethylstearylammonium chloride; about 4 weight percent glycerin; about 4 weight percent propylene glycol; about 0.2 weight percent tetra sodium ethylene diamine tetra acetic acid; about 0.4 weight percent sodium sulfite; about 0.2 weight percent ascorbic acid; about 1.4 weight percent ammonium; about 1 weight percent ammonium hydrogen carbonate; from 0.2 to 2 weight percent or one or more of aminoethylaminopropylmethyl siloxane-dimethylsiloxane copolymer and dimethyldiallylammonium chloride-acrylic acid copolymer solution at 38%; about 0.2 weight percent perfume; about 1 weight percent sulfuric acid toluene-2,5-diamine; about 0.5 weight percent resorcin; from 0.7 to 1 weight percent or one or more of succinic acid and sodium succinate; about 0.6 weight percent potassium hydroxide; about 0.3 weight percent amino methyl propanol; and water.

2. A first agent of an oxidative hair dye or a hair bleaching agent comprising:
(A) a polyvalent carboxylic acid having no hydroxyl group or a salt of the polyvalent carboxylic acid having no hydroxyl group;
(B) a surfactant comprising (B1) a cationic surfactant and (B2) a nonionic surfactant, wherein the cationic surfactant (B1) is selected from the group of lauryl trimethyl ammonium chloride, stearyl trimethylammonium chloride, cetyl trimethylammonium chloride, behenyl trimethyl ammonium chloride, distearyl trimethyl ammonium chloride, cetyl trimethyl ammonium bromide, stearyl trimethyl ammonium chloride bromide, benzalkonium chloride, tri (polyoxyethylene) stearyl ammonium chloride, and combinations thereof; and the nonionic surfactant (B2) is selected from the group of polyoxyethylene (POE) alkyl ethers, POE alkyl phenyl ethers, POE polyoxypropylene alkyl ethers, POE sorbitan fatty acid esters, POE propylene glycol fatty acid esters, and combinations thereof;
(C) an oily component; and
(D) an alkaline agent, wherein the first agent comprises about 6 weight percent cetostearyl alcohol; about 4 weight percent liquid paraffin; about 3 weight percent polyoxyethylene cetostearyl ether with about 30 ethylene oxide adducts; about 1 weight percent polyoxyethylene cetostearyl ether with about 6 ethylene oxide adducts; about 2.5 weight percent polyoxyethylene stearyl ether with 100 ethylene oxide adducts; about 1.6 weight percent of trimethylstearylammonium chloride; about 4 weight percent glycerin; about 4 weight percent propylene glycol; about 0.2 weight percent tetra sodium ethylene diamine tetra acetic acid; about 0.4 weight percent sodium sulfite; about 0.2 weight percent ascorbic acid; about 1.4 weight percent ammonium; about 1 weight percent ammonium hydrogen carbonate; about 1 weight percent or one or more of aminoethylaminopropylmethyl siloxane-dimethylsiloxane copolymer and dimethyldiallylammonium chloride-acrylic acid copolymer solution at 38%; about 0.2 weight percent perfume; about 1 weight percent sulfuric acid toluene-2,5-diamine; about 0.5 weight percent resorcin; from 0.7 weight percent succinic acid; about 0.6 weight percent potassium hydroxide; about 0.3 weight percent amino methyl propanol; and water.

3. A first agent of an oxidative hair dye or a hair bleaching agent comprising:
(A) a polyvalent carboxylic acid having no hydroxyl group or a salt of the polyvalent carboxylic acid having no hydroxyl group;
(B) a surfactant comprising (B1) a cationic surfactant and (B2) a nonionic surfactant, wherein the cationic surfactant (B1) is selected from the group of lauryl trimethyl ammonium chloride, stearyl trimethylammonium chloride, cetyl trimethylammonium chloride, behenyl trimethyl ammonium chloride, distearyl trimethyl ammonium chloride, cetyl trimethyl ammonium bromide, stearyl trimethyl ammonium chloride bromide, benzalkonium chloride, tri (polyoxyethylene) stearyl ammonium chloride, and combinations thereof; and the nonionic surfactant (B2) is selected from the group of polyoxyethylene (POE) alkyl ethers, POE alkyl phenyl ethers, POE polyoxypropylene alkyl ethers, POE sorbitan fatty acid esters, POE propylene glycol fatty acid esters, and combinations thereof;
(C) an oily component; and
(D) an alkaline agent, wherein the first agent comprises about 6 weight percent cetostearyl alcohol, about 4 weight percent liquid paraffin, about 3 weight percent polyoxyethylene cetostearyl ether with about 30 ethylene oxide adducts, about 1 weight percent polyoxyethylene cetostearyl ether with about 6 ethylene oxide adducts, about 2.5 weight percent polyoxyethylene stearyl ether with 100 ethylene oxide adducts, about 1.6 weight percent of trimethylstearylammonium chloride, about 4 weight percent glycerin, about 4 weight percent propylene glycol, about 0.2 weight percent tetra sodium ethylene diamine tetra acetic acid, about 0.4 weight percent sodium sulfite, about 0.2 weight percent ascorbic acid, about 1.4 weight percent ammonium, about 1 weight percent ammonium hydrogen carbonate, about 1 weight percent aminoethylaminopropylmethyl siloxane dimethylsiloxane copolymer, about 0.2 weight percent perfume, about 1 weight percent sulfuric acid toluene-2,5-diamine, about 0.5 weight percent resorcin, about 0.7 weight percent succinic acid, about 0.6 weight percent potassium hydroxide, about 0.3 weight percent amino methyl propanol, and water.

\* \* \* \* \*